(12) United States Patent
Smith et al.

(10) Patent No.: US 6,409,754 B1
(45) Date of Patent: Jun. 25, 2002

(54) FLEXIBLE SEGMENTED STENT

(75) Inventors: Scott R. Smith, Chaska; Douglas P. Killion, Maple Grove, both of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/346,826

(22) Filed: Jul. 2, 1999

(51) Int. Cl.$^7$ .................................................. A61F 2/06
(52) U.S. Cl. ..................................... 623/1.16; 623/1.46
(58) Field of Search .............................. 623/1.16, 1.15, 623/1.18, 1.2, 1.46; 606/198, 191, 195

(56) References Cited

U.S. PATENT DOCUMENTS

| | | | |
|---|---|---|---|
| 5,035,706 A | 7/1991 | Giantureo et al. | 606/198 |
| 5,104,404 A | 4/1992 | Wolff | 623/1 |
| 5,135,536 A | 8/1992 | Hillstead | 606/915 |
| 5,282,824 A | 2/1994 | Gianturco | 606/198 |
| 5,405,377 A | 4/1995 | Cragg | 623/1 |
| 5,443,496 A | 8/1995 | Schwartz et al. | 623/1 |
| 5,449,373 A * | 9/1995 | Pinchasik et al. | 606/198 |
| 5,507,771 A | 4/1996 | Gianturco | 606/198 |
| 5,540,712 A | 7/1996 | Kleshinski et al. | 606/198 |
| 5,601,593 A | 2/1997 | Freitag | 606/198 |
| 5,683,450 A | 11/1997 | Goicoechea et al. | 623/1 |
| 5,741,327 A | 4/1998 | Frantzen | 623/1 |
| 5,776,162 A | 7/1998 | Kleshinski | 606/198 |
| 5,800,456 A | 9/1998 | Maeda et al. | 606/198 |
| 5,807,404 A * | 9/1998 | Richter | 623/1.16 |
| 5,817,126 A | 10/1998 | Imran | 606/198 |
| 5,843,175 A | 12/1998 | Frantzen | 623/1 |
| 5,902,317 A | 5/1999 | Kleshinski et al. | 606/198 |
| 5,938,697 A | 8/1999 | Killion et al. | 623/1 |
| 6,066,168 A * | 5/2000 | Lau et al. | 623/1.16 |
| 6,231,598 B1 * | 5/2001 | Berry et al. | 623/1.15 |
| 6,264,687 B1 | 7/2001 | Tomonto | 623/1.16 |

FOREIGN PATENT DOCUMENTS

| | | |
|---|---|---|
| EP | 0 541 443 A1 | 5/1993 |
| WO | 95/31945 | 11/1995 |
| WO | 98/20810 | 5/1998 |
| WO | 99/60953 | 12/1999 |

OTHER PUBLICATIONS

"Modified Gianturco Expandable Wire Stents in Experimental And Clinical Use" by J. Rosch et al, CIRSE, Porto Cervo, Sardinia, May 25–29, 1987, pp. 100–103.

* cited by examiner

*Primary Examiner*—Kevin T. Truong
(74) *Attorney, Agent, or Firm*—Vidas, Arrett & Steinkraus

(57) ABSTRACT

A radially expandable segmented stent having plastic, i.e., permanent deformation, connectors interconnecting each segment.

30 Claims, 3 Drawing Sheets

FLEXIBLE SEGMENTED STENT

BACKGROUND OF THE INVENTION

This invention relates to multiple interconnected stents or stent segments, the interconnections being comprised of lengths of a plastic material. The term "plastic" is used herein to refer to materials which are capable of being deformed permanently without rupture.

In the prior art, stents are well known for use in opening and reinforcing the interior wall of blood vessels and other body conduits.

Stents are generally tubular, radially expandable and may be of the self-expanding type or may be expandable with an outward pressure applied to the stent, typically by expansion of an interiorly positioned balloon. Stents are made of various materials such as plastic or metal, metal usually being preferred.

Since stents must be of somewhat rigid design to provide reinforcement support and may be required to be of considerable length in order to extend over a lengthy area, it is difficult to resolve this need for rigidity with the need for having a flexible stent which is readily implanted by inserting it through a sometimes tortuous curving path as is often encountered in the percutaneous insertion technique typically used for implantation of stents. This is further complicated by the fact that stents must be readily expandable upon implantation to provide a support structure.

It is known that a plurality of stent elements can be loosely interconnected together by filaments or the like to provide a lengthy flexible stent arrangement. Such arrangements are shown in the following patents for example:

U.S. Pat. No. 5,405,377 to Cragg
U.S. Pat. No. 5,665,115 to Cragg
U.S. Pat. No. 5,755,781 to Jayaraman
U.S. Pat. No. 5,443,476 to Schwartz et al.
U.S. Pat. No. 5,135,536 to Hillstead
U.S. Pat. No. 5,035,706 to Gianturco et al.
WO 93/13825 (PCT) to Maeda et al.

The following technical literature is also of interest in this regard:

Tracheobronchial Tree: Expandable Metallic Stents Used in Experimental and Clinical Applications, Work in Progress; *Radiology*, February 1986, pp 309–312.

Experimental intrahepatic Portacaval Anastomosis: Use of Expandable Gianturco Stents; *Radiology*, February 1987, 162: 481–485.

Gianturco Expandable Wire Stents in the Treatment of Superior Vena Cava Syndrome Recurring After Maximum—Tolerance Radiation; *Cancer*, September 1987, Vol. 60, pp 1243–1246.

Modified Gianturco Expandable Wire Stents in Experimental And Clinical Use; *Cerise*, Porto Cervo, May 1987, pp 100–103.

BRIEF SUMMARY OF THE INVENTION

This invention is directed to an improvement in the general concept of joined stents or stent segments (hereinafter referred to collectively as "stent segments") in which a "plastic" material (capable of exhibiting permanent deformation) extends between stents or stent segments (hereinafter referred to collectively as stent segments) to interconnect them with a somewhat constrained freedom of motion relative to each other, i.e., not loosely connected but flexibly connected. The stent segments are preferably of closed cell design and even more preferably of the self-expanding type. More precisely, the interconnecting elements are of a material different than the stent material and are plastically deformable.

BRIEF DESCRIPTION OF THE DRAWING(S)

DESCRIPTION OF THE PREFERRED EMBODIMENTS

Figure 1:
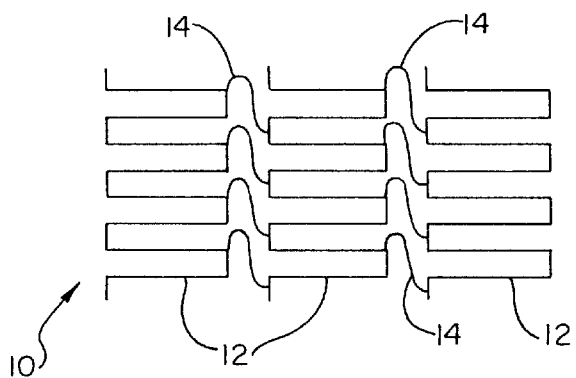
FIG. 1 is a schematic showing of a stent according to the invention.

Referring to FIG. 1, a schematic drawing of a flexible segmented stent 10 according to the invention is shown. It is preferably comprised of a plurality of closed cell stents or stent segments 12 interconnected by plastic connectors 14.

Stents 12 are most preferably of closed cell construction and of the self-expandable type such as NITINOL stents which are cut or etched from tubular stock or rolled from cut or etched flat sheet or other shape memory metals which do not themselves exhibit permanent deformation.

Generally speaking, a self-expanding stent tends to return to its unconstrained or expanded condition. Also, in this type of stent it is generally preferred that it be of a closed cell construction. In accordance with this invention it has been found to be particularly advantageous to use self-expanding elastic material for the stent or stent segment, i.e., a material which is not "plastic" or "deformable" and to use a "plastic" "deformable" material for the connector elements. Such materials as plastic, i.e., polymeric, which may be biodegradable, metals such as gold, or viscoelastic polymers such as polyethylene may be used. Such connectors provide constrained motion yet some flexibility of the stent portions relative to each other and allow for permanent expansion of the combination as needed.

Alternatively, the stents may be of the type which are expandable with an outward radial pressure as is known in the art and may be of closed cell or open cell construction. Such stents may be of metal such as stainless steel, titanium, nickel or any other metal compatible with the body. However, in this type of combination, the connector elements will, according to the invention, be of a different material than the stents or stent segments yet the connector elements will be of a "plastic", i.e., deformable material such as a polymer or the like as pointed out above.

In use, these stent combinations will allow for the provisions of relatively long stents which may be trimmed to any desired length at the time of the procedure.

Figure 2:
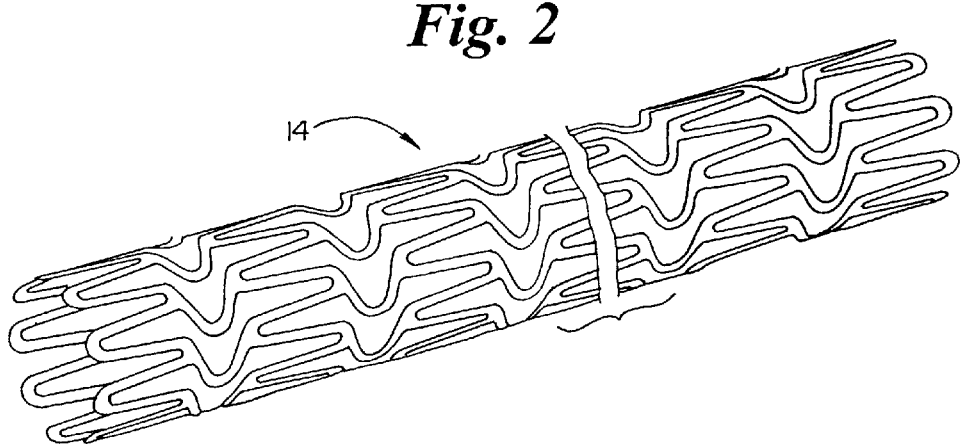
FIG. 2 is a schematic showing of a closed cell stent.
Figure 3:
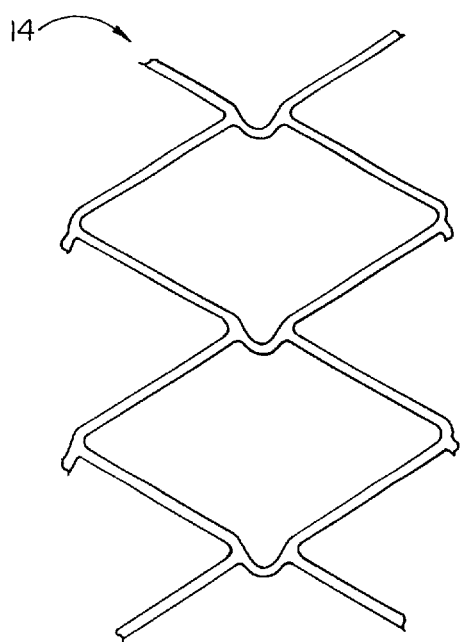
FIG. 3 shows the stent of FIG. 2 expanded in a fragmentary view.

FIG. 2 is a specific example of one type of closed cell construction in a stent 14. FIG. 3 shows the closed cells of stent 14 when expanded.

Figure 4:
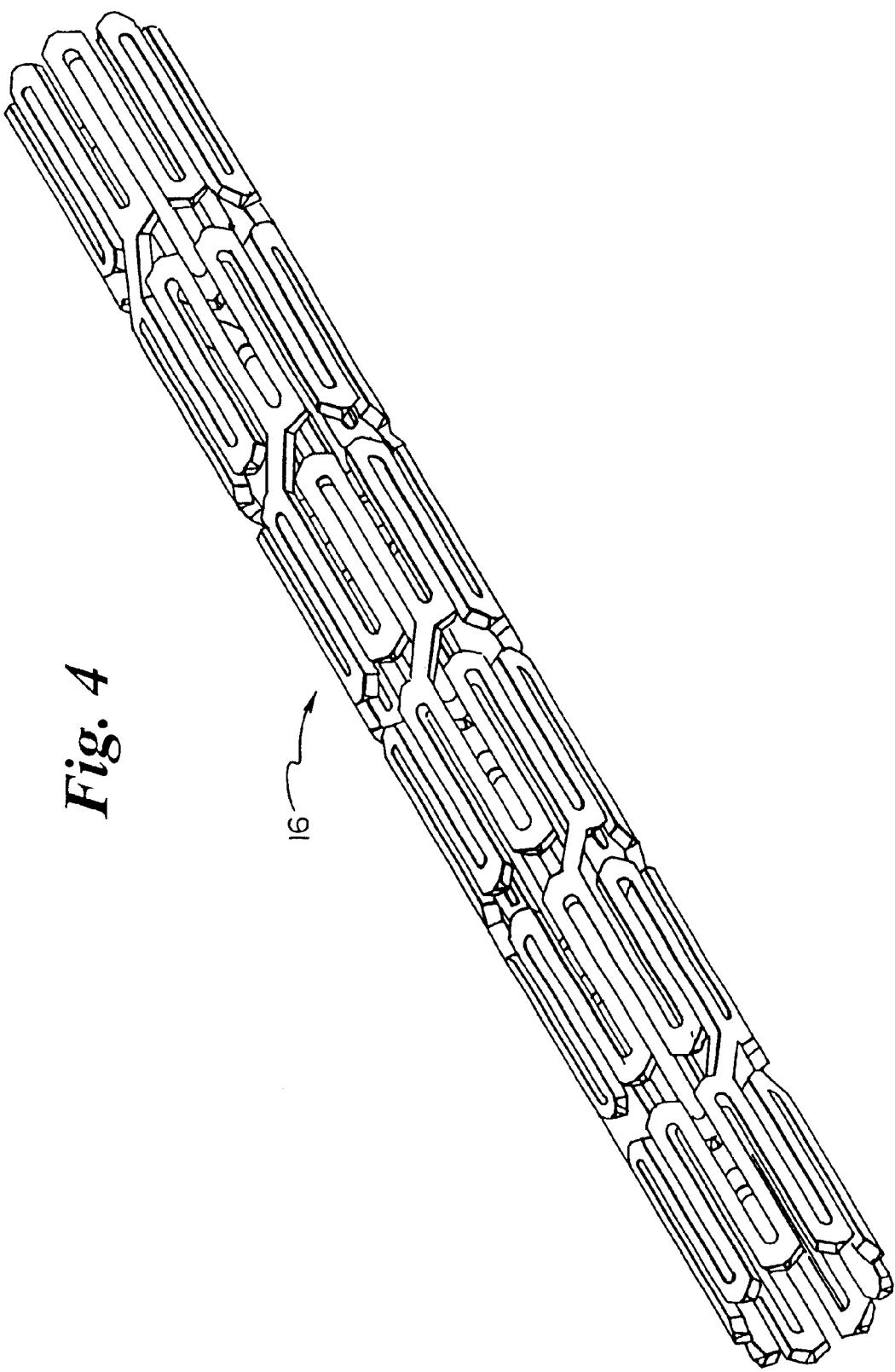
FIG. 4 is a schematic showing of an open cell stent.
Figure 5:
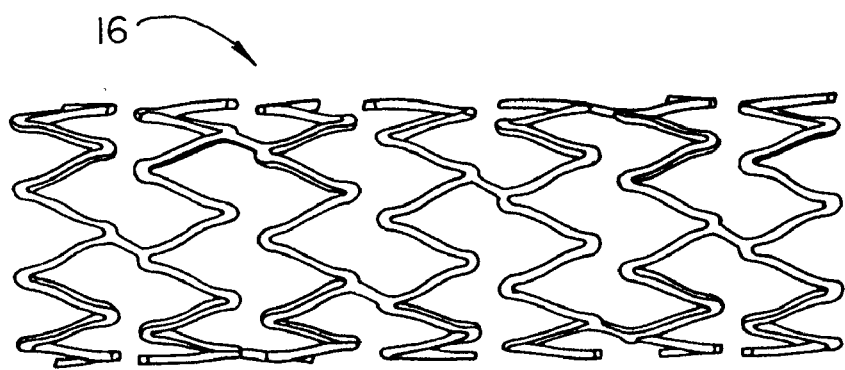
FIG. 5 shows the stent of FIG. 4 expanded.

FIG. 4 is an example of open cell construction in a stent 16. FIG. 5 shows the open cells of stent 16 when expanded.

In one embodiment of the invention, it relates to self expanding stents or stent segments interconnected by connector elements of a different material exhibiting permanent deformation, i.e., "plastic behavior" upon expansion, the stents preferably being of closed cell construction.

In another embodiment of the invention it relates to balloon expandable or the like stents or stent segments rigidly interconnected by structural connector elements of a different "plastic" material than the stents or stent segments, preferably polymeric plastic, most preferably biodegradable, although in the case of a metal stent, the connector may be of a different metal exhibiting different permanent deformation characteristics, i.e., plastic behavior.

Connector elements may be of any of the variety of implantable grade metals or polymeric plastics such as polytetrafluoroethylene, polyethylene, polypropylene, nylon, polyester, polyurethane and others exhibiting permanent deformation and of a material different from that of the stent or stent segment per se.

The connector elements may also be of biodegradable material such as polycaprolactone, polyglycolic acid, polylactic acid and the like, so long as the material exhibits permanent deformation and form a structural part of the stent combination.

If the stents are of metal they may be coated with a biocompatible material such as polyurethane, polyethylene, polytetrafluorethylene, silicone, block copolymers of polyurethane, polyethylene and silicone, biodegradable polymers such as polylactic acid, polyglycollic acid and/or hydroxy butyrate or valerate copolymer.

In such an instance, the connectors may be fused to the coating on each stent segment to interconnect them.

Figure 6:
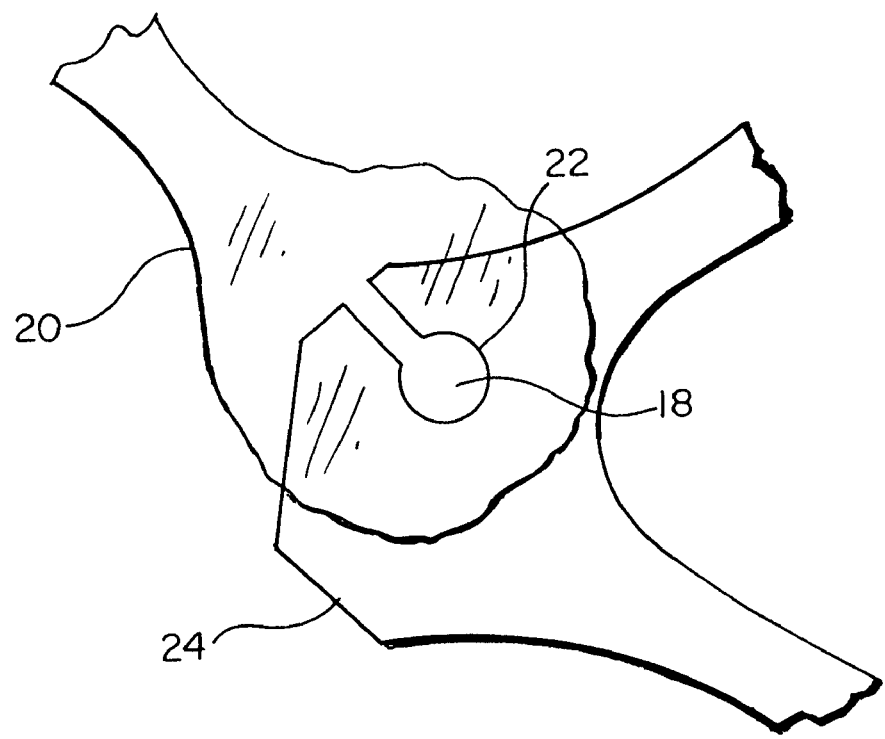
FIG. 6 is a showing of a preferred connection arrangement for a stent of the invention.

Most preferably however, interconnection between stents is accomplished as shown in FIG. 6. In such an arrangement, a raised portion 18 is formed on connector 20 and an opening 22 is formed in stent 24, the opening 22 being shaped to receive portion 18 and interfit therewith. Of course, the reverse arrangement may be used in which the received portion 18 is on stent 22 and the opening 22 is on the connector 20.

The connectors are preferably flat and elongated but may be of various configurations such as straight, S-shaped, U-shaped, etc., and of different cross-section.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A segmented stent comprising a plurality of generally annular and radially expandable stent segments, segments which are adjacent to one another being interconnected by at least one interconnector element of a plastically deformable material wherein the stent segments are made of a material which does not exhibit permanent deformation.

2. The segemented stent of claim 1 wherein the stent segments are of closed cell construction.

3. The segmented stent of claim 1 wherein the stent segments are coated with a polymeric material and the interconnector elements of plastically deformable material are fused to the polymeric material.

4. The segmented stent of claim 3 wherein the polymeric material and the interconnector elements of plastically deformable material are of different composition.

5. The segmented stent of claim 1 including at least one segment having at least one anchor point means for receiving one of the interconnector elements and the interconnector element received by the anchor point means includes interfitting means for connection to the anchor point means.

6. The segmented stent of claim 5 wherein the anchor point means forms a raised portion and the interfitting means on the interconnector element comprises an opening sized to fit over the anchor point means and interlock therewith.

7. The segmented stent of claim 5 wherein the interconnector element includes at each end a raised portion and the stent segments each include at least one opening sized to receive a raised portion and interlock therewith.

8. The segmented stent of claim 1 wherein each stent segment is designed and arranged as an independent stent body capable of individual support in a body vessel.

9. The segmented stent of claim 1 wherein the interconnector elements are biodegradable.

10. The segmented stent of claim 1 wherein the stent segments are of closed cell construction and are self-expandable.

11. A segmented stent comprising a plurality of generally annular and radially expandable stent segments, segments which are adjacent one another being interconnected by at least one interconnector element of a plastically deformable material having deformation properties which differ from those of the segments to provide flexible yet constrained relative motions between the stent segments wherein the stent segments are of self-expanding construction.

12. The segmented stent of claim 11 wherein the stent segments are of a shape memory material.

13. A segmented stent comprising a plurality of generally annular and radially expandable stent segments, segments which are adjacent one another being interconnected by at least one interconnector element of a plastically deformable material to provide flexible yet constrained relative motions between the stent segments wherein the stent segments are of balloon expandable construction and are of metal and the interconnector elements are of a different metal, exhibiting different permanent deformation characteristics than the stent segments.

14. A stent comprising a plurality of generally annular and radially self-expanding stent segments, segments which are adjacent one another being interconnected by at least one interconnector element of a viscoelastically deformable material to provide flexible yet constrained relative motions between the stent segments.

15. The segmented stent of claim 14 wherein the stent segments are of closed cell construction.

16. The segmented stent of claim 14 wherein the stent segments are of balloon expandable construction and are of metal and the interconnector elements are of a different metal, exhibiting different permanent deformation characteristics than the stent segments.

17. The segmented stent of claim 14 wherein each stent segment is designed and arranged as an independent stent body capable of individual support in a body vessel.

18. The segmented stent of claim 14 wherein the interconnector elements are biodegradable.

19. The segmented stent of claim 14 wherein the stent segments are of closed cell construction and are self-expandable.

20. A stent comprising a plurality of generally annular and radially expandable metal stent segments of non-viscoelastically deformable material, segments which are adjacent one another being interconnected by at least one interconnector element of a viscoelastically deformable material to provide flexible yet constrained relative motions between the stent segments.

21. The segmented stent of claim 20 wherein the stent segments are of a shape memory material.

22. The segmented stent of claim 20 wherein the stent segments are coated with a polymeric material and the interconnector elements are fused to the polymer coating.

23. The segmented stent of claim 22 wherein the polymeric material and the interconnectors are of different compositions.

24. The segmented stent of claim 20 including at least one segment having at least one anchor point means for receiving one of the interconnector elements and the interconnector element received by the anchor point means includes interfitting means for connection to the anchor point means.

25. The segmented stent of claim 24 wherein the anchor point means forms a raised portion and the interfitting means on the interconnector comprises an opening sized to fit over the anchor point means and interlock therewith.

26. The segmented stent of claim 24 wherein the interconnector includes at each end a raised portion and the stent segments each include at least one opening sized to receive a raised portion and interlock therewith.

27. The segmented stent of claim 24 wherein the interconnector elements are of polymeric material.

28. An expandable stent comprising a plurality of generally annular stent segments made of a first material, segments which are adjacent one another being interconnected by at least one interconnector element of a second material having different deformation properties from the first material, the first material being a shape memory material and the second material plastically deformable.

29. The stent of claim 28 wherein the shape memory material is a shape memory metal.

30. An expandable stent comprising a plurality of generally annular stent segments including a first annular segment and a second annular segment, the first and second annular segments made of a first material and interconnected by at least one interconnector element of a second material, the second material of different composition from the first material.

* * * * *